United States Patent [19]
Mayenberger

[11] Patent Number: 5,910,153
[45] Date of Patent: Jun. 8, 1999

[54] SURGICAL PUNCH

[75] Inventor: Rupert Mayenberger, Rielasingen, Germany

[73] Assignee: Aesculap AG & Co. KG, Tuttlingen, Germany

[21] Appl. No.: 08/984,906

[22] Filed: Dec. 4, 1997

[30] Foreign Application Priority Data

Dec. 4, 1996 [DE] Germany .......................... 196 50 204

[51] Int. Cl.⁶ .................................................. A61B 17/32
[52] U.S. Cl. .......................................................... 606/184
[58] Field of Search ..................... 606/184, 167, 606/171, 185, 174, 170; 604/22; 30/263, 240

[56] References Cited

U.S. PATENT DOCUMENTS

| | | | |
|---|---|---|---|
| 3,837,345 | 9/1974 | Matar | 606/184 |
| 4,018,228 | 4/1977 | Goosen . | |
| 5,129,913 | 7/1992 | Ruppert . | |
| 5,192,294 | 3/1993 | Blake, III | 606/184 |
| 5,350,392 | 9/1994 | Purcell et al. . | |

FOREIGN PATENT DOCUMENTS

| | | |
|---|---|---|
| 124454 | 4/1931 | Austria . |
| 1 160 573 | 1/1964 | Germany . |

Primary Examiner—Michael Buiz
Assistant Examiner—Vikki Trinh
Attorney, Agent, or Firm—Barry R. Lipsitz; Ralph F. Hoppin

[57] ABSTRACT

To allow easy replacement of tools in a surgical punch with a tubular shaft, the distal end of which forms an annular cutting edge, a cutting member is mounted for longitudinal displacement in relation to the shaft, interacts with a cutting edge, and is held on an advancing element mounted for displacement in the shaft. An actuating member, arranged at the proximal end of the shaft, displaces the advancing element in the shaft. The cutting member is releasably connected to the advancing element and/or a sleeve bearing the cutting edge to the shaft. The releasable connections are provided using radially and elastically displaceable projections or detents on one part which engage behind recesses on the other part in a locking position and thereby secure the parts inserted into one another in an axial direction against any separation. The detents are prevented from moving radially out of the locking position into a release position by the abutment of the cutting member and advancing element on the inner wall of the shaft and/or the sleeve in the region of the detents. The advancing element and the cutting member are displaceable in an axial direction after release of the connection to the actuating member to such an extent in relation to the shaft that the radial movement of the detents into the release position is no longer hindered.

33 Claims, 5 Drawing Sheets

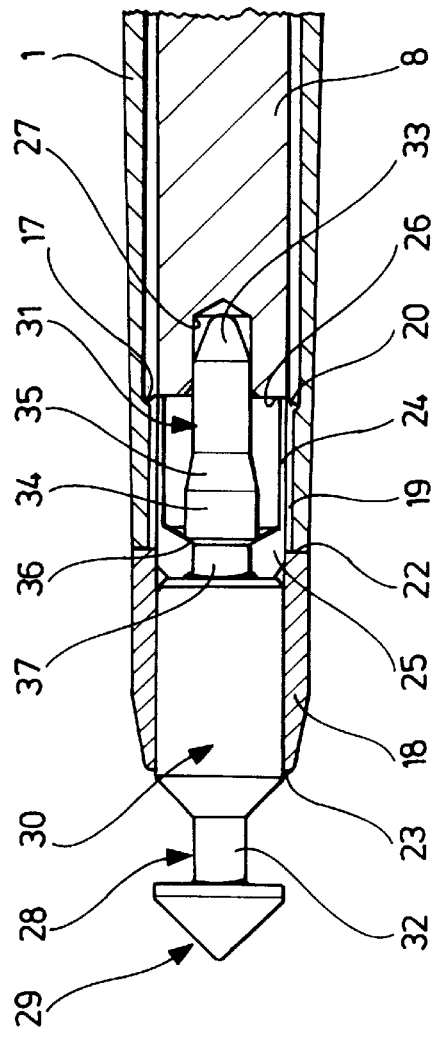
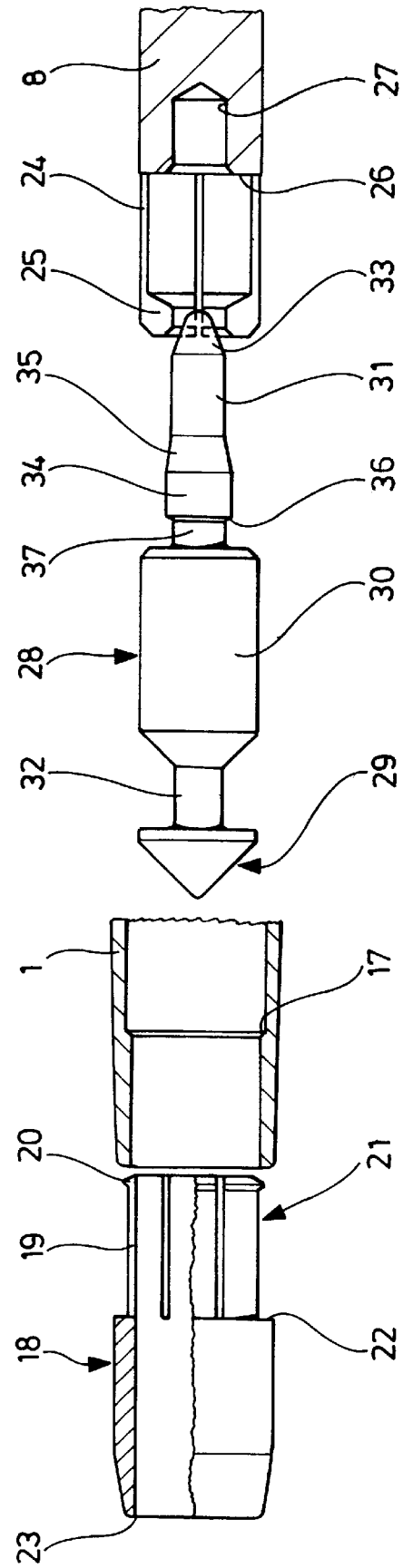
FIG. 3
FIG. 4

SURGICAL PUNCH

BACKGROUND OF THE INVENTION

The invention relates to a surgical punch with a tubular shaft, the distal end of which forms an annular cutting edge, a cutting member which is mounted for longitudinal displacement in relation to the shaft, interacts with the cutting edge and is held on an advancing element mounted for displacement in the tube, and an actuating member for displacing the advancing element in the shaft, this member being arranged at the proximal end of the shaft.

Surgical punches of this type are used to introduce openings into vascular walls, for example for attaching a bypass vessel. In this respect, a cutting member which can, for example, be of a conical design is brought close to a cutting edge with its circumferential edge, wherein the vascular wall is entrained between cutting member and cutting edge. As a result, a cut is made in the vascular wall along the cutting edge, i.e. circular openings can, for example, be introduced into vascular walls.

In the case of conventional instruments, a different punch has to be used for each opening size; moreover, these instruments can be used only for such a time as the cutting edge of the cutting member generates a clean cut, i.e. the cutting edge has the desired sharpness and is not damaged in any way. If the cutting edge becomes blunt or damaged, the instrument has to be replaced.

SUMMARY OF THE INVENTION

The object of the invention is to design a generic punch such that it can be adapted in a simple manner to different cutting geometries and/or can be made operable again by replacing the cutting member and/or the cutting edge.

This object is accomplished in accordance with the invention, in a surgical punch of the type described at the outset, in that the cutting member is releasably connected to the advancing element and/or a sleeve bearing the cutting edge to the shaft, that the releasable connection is provided each time by means of radially and elastically displaceable detents on one part which engage behind recesses on the respectively other part in a locking position and thereby secure the parts inserted into one another in axial direction against any separation, that the detents are prevented from moving radially out of the locking position engaging behind the recesses into a release position as a result of the abutment of the unit consisting of cutting member and advancing element on the inner wall of the shaft and, where applicable, the sleeve in the region of the detents and that the advancing element and the cutting member are displaceable in axial direction after release of the connection to the actuating member to such an extent in relation to the shaft that the radial movement of the detents into the release position is no longer hindered.

It is, therefore, provided either for the cutting member to be separable from the advancing element and replaceable or for the shaft to bear at its front end a separable sleeve, the free edge of which is designed as a cutting edge. While these measures can be provided alternatively, it is particularly advantageous when both measures are realized at the same time.

The connections of the sleeve to the shaft and of the cutting member to the advancing element are, in both cases, provided by means of elastic detents which can be displaced in radial direction like a collet. This displacement into the release position is only possible when the advancing element is displaced in a proximal direction in relation to the shaft, i.e. in the direction towards the actuating member. The displacement is thereby greater than the displacement which the advancing element undergoes during normal operation, during which the cutting member is also displaced in a proximal direction during displacement of the advancing element until it abuts on the cutting edge and, where applicable, is moved slightly past this. Only when the advancing element is displaced even further in a proximal direction will the detents be released, and it is only then possible to remove the cutting member and/or the sleeve while the detents are displaced radially and elastically.

A release of the detents is possible in any case when the advancing element is withdrawn completely in a proximal direction out of the shaft since the advancing element can then no longer abut on the detents.

In a preferred embodiment, it is, however, provided for the advancing element and the cutting member to be displaceable in axial direction after release of the connection to the actuating member to such an extent in relation to the shaft that a recessed section of the shaft and the advancing element, respectively, is arranged in the region of the detents, this section making a radial movement of the detents into the release position possible. In this case, a radial movement of the detents is already made possible as a result of the recessed sections in the shaft or in the advancing element when the detents and the shaft or the advancing element are still located opposite one another, i.e. the advancing element has not been withdrawn completely out of the shaft in proximal direction. On account of the recessed sections, the detents can, however, still be moved into the release position in this case. It is therefore sufficient for their release to move the advancing element in proximal direction a certain distance into the shaft; a complete withdrawal is not then necessary.

It is favorable when the detents are designed as flexible tongues extending axis parallel and distributed over the circumference, these flexible tongues bearing a laterally protruding detent projection at the free end.

In accordance with a preferred embodiment, it may be provided for the flexible tongues to be arranged on the sleeve and form an insert shaft which is insertable into the shaft of the punch. These flexible tongues thus undertake a double function, namely, on the one hand, the fixing of the sleeve on the shaft in a radial direction and, on the other hand, a fixing in position in axial direction, as well, as a result of their locking in and engagement behind the recesses.

The flexible tongues can be designed, in particular, in one piece with the sleeve.

It is favorable when the recess on the shaft is formed by an annular shoulder on the inner wall adjoined in proximal direction by a section, the internal diameter of which is greater than in the section distally of the annular shoulder. This section with a greater internal diameter enables the detents which connect the cutting member to the advancing element to spring out and thus to release the cutting member from the advancing element even when the advancing element is not completely withdrawn rearwards out of the shaft.

It can furthermore be provided for the flexible tongues to be arranged on the advancing element and in the locking position engage in an annular groove of the cutting member with the inwardly directed detent projection. In this case, as well, the flexible tongues can be designed, in particular, in one piece with the advancing element.

The flexible tongues thereby form a sleeve or a cage which surrounds the cutting member on its circumferential side and centers it. This centering can also be improved by the cutting member dipping with a proximal extension into a central, end-face recess of the advancing element. This recess is thus located on the base of the sleeve-like cage which is formed by the flexible tongues.

In a particularly preferred embodiment it is provided for the detents of the cutting member and the detents of the sleeve to abut on one another in operative position of the punch and thereby prevent one another from moving into the release position. When shaft and advancing element are displaced in axial direction relative to one another to such an extent that the detents no longer abut on one another, these can respectively spring out into the release position.

It is also advantageous when the cutting member has a cylindrical guide section which abuts in operative position on the inner wall of the shaft or, where applicable, the sleeve whilst guiding the cutting member. It is thus ensured that the cutting member is guided exactly in relation to the shaft during its operative movement and is thereby brought closer to the cutting edge in a completely uniform manner.

In a preferred embodiment it is provided for the actuating member to be a hand lever articulatedly connected to the shaft and releasably connected to the advancing element via a hinge connection.

The hand lever can be designed as a branch which is pivotable against a stationary branch rigidly connected to the shaft.

According to a preferred embodiment, the releasable hinge connection between hand lever and advancing element is formed by a hinge pin mounted on one of the parts for axial displacement, this pin having sections with different diameters in axial direction, wherein the section with a smaller diameter passes through a radial insert slot of a hinge opening on the one part receiving the hinge pin, the section with a larger diameter, on the other hand, does not. As long as the section with a larger diameter is located in the hinge opening, the actuating member is pivotally mounted on the shaft. If, on the other hand, the hinge pin is displaced such that the section with a smaller diameter projects into the hinge opening, it is possible to withdraw the part having the hinge opening from the hinge pin in the direction of the insert slot and thus separate the advancing element from the actuating member so that the advancing element can be freely displaced in relation to the shaft.

Surgical instruments of the type described normally have small outer dimensions, in particular, transversely to the longitudinal direction. In order, nevertheless, to make a satisfactory mounting of the actuating members on the shaft possible and, nevertheless, to make the insertion of the advancing element from the proximal side possible, it may be provided for the actuating member to be mounted on the rear side of the shaft on one side thereof and for an opening, through which the advancing element is inserted, to lead into the interior of the shaft on the other side next to its mounting. The actuating member and the opening are therefore arranged next to one another. This can have the effect that, according to a preferred embodiment, the opening is offset laterally in relation to the central plane of the shaft.

It may, nevertheless, be provided for the cutting edge to be arranged symmetrically to the central plane of the shaft and for the advancing element to extend slightly inclined in relation to the longitudinal central plane of the shaft. This slight inclination is innocuous since the cutting member is guided in the shaft at the distal end thereof and since the slight inclination can easily be absorbed as a result of the elasticity of the advancing element.

Whereas it is possible to design the cutting member and the sleeve as independent parts which can be removed from the shaft and the advancing element, respectively, independently of one another in the manner described, it may be provided in a preferred embodiment for the cutting member to be mounted in the sleeve so as to be longitudinally displaceable and undetachable. In this case, sleeve and cutting member thus form a structural unit which can be detached from the surgical punch. The two parts are, however, connected to different parts of this punch, namely the sleeve still to the shaft and the cutting member still to the advancing element. The two connecting points are displaceable relative to one another, and it is therefore advantageous when these connecting points are designed in the manner described as detent connections which are locked in the manner described in the normal operating range but can be released as a result of axial displacement of the shaft in relation to the advancing element over a greater distance.

It is favorable with such a unit when the cutting member in the sleeve is acted upon in proximal direction by a spring and when the path of displacement to be covered under the action of this spring is limited by a stop. This means that the delicate cutting member is drawn into the interior of the sleeve when this structural unit is removed from the punch. Moreover, it is thus ensured that the cutting member can form a detent connection with the advancing element in the manner described when the structural unit is inserted into the punch and is displaced out of the sleeve in distal direction not only during touching of the advancing element.

The following description of preferred embodiments of the invention serves to explain the invention in greater detail in conjunction with the drawings.

DETAILED DESCRIPTION OF THE DRAWINGS

Figure 1:
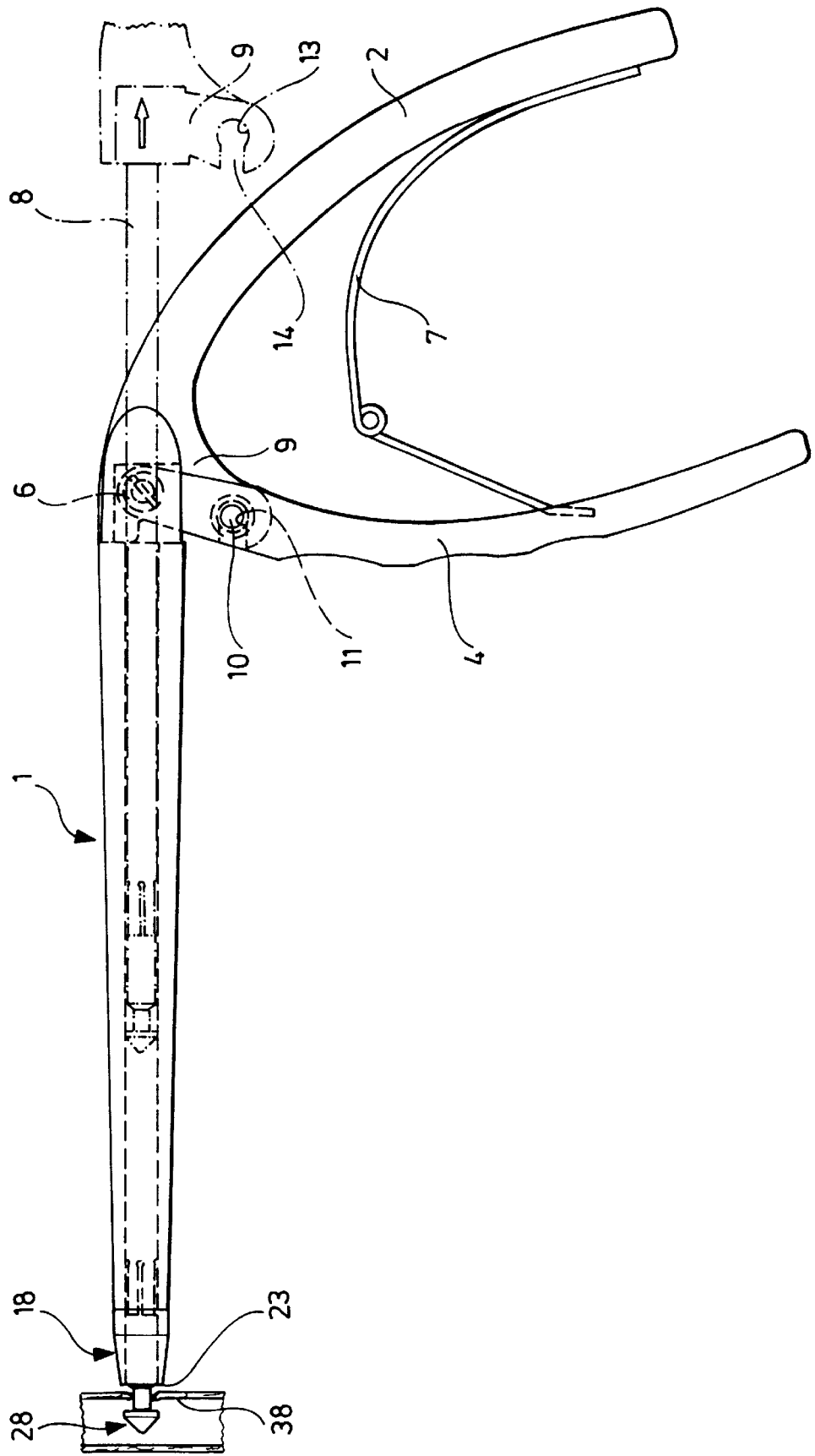
Figure 2:
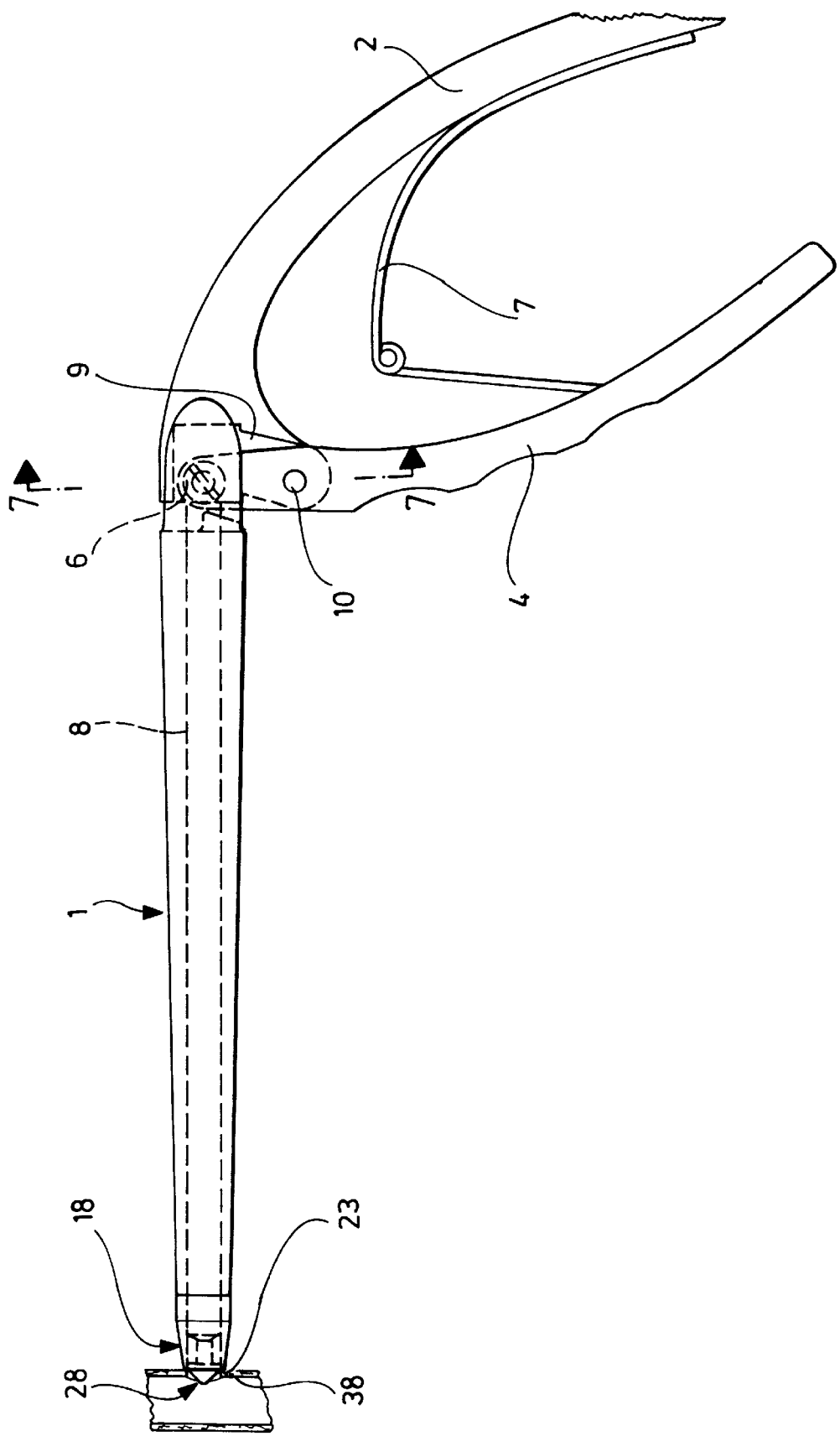
Figure 5:
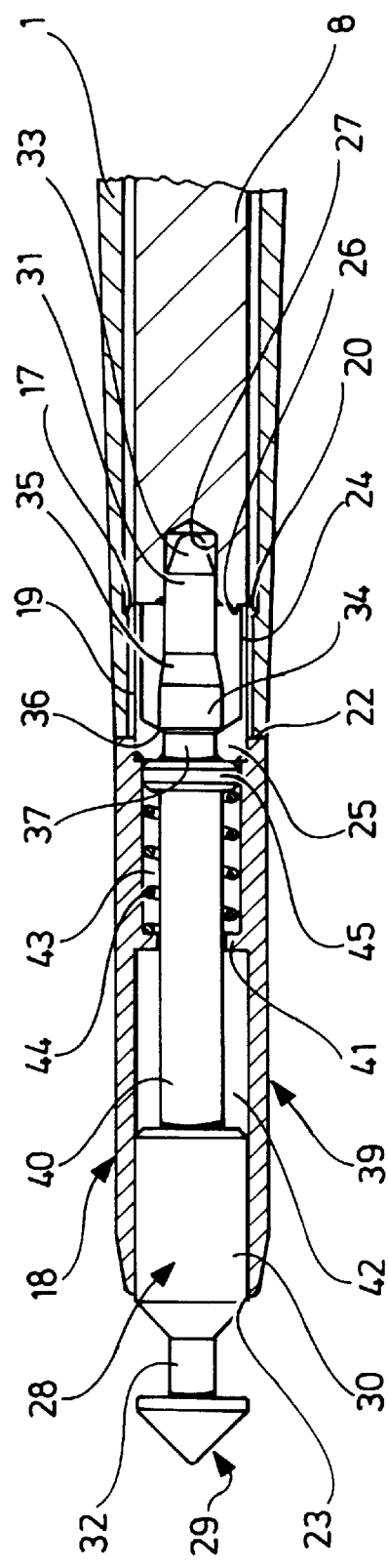
Figure 6:
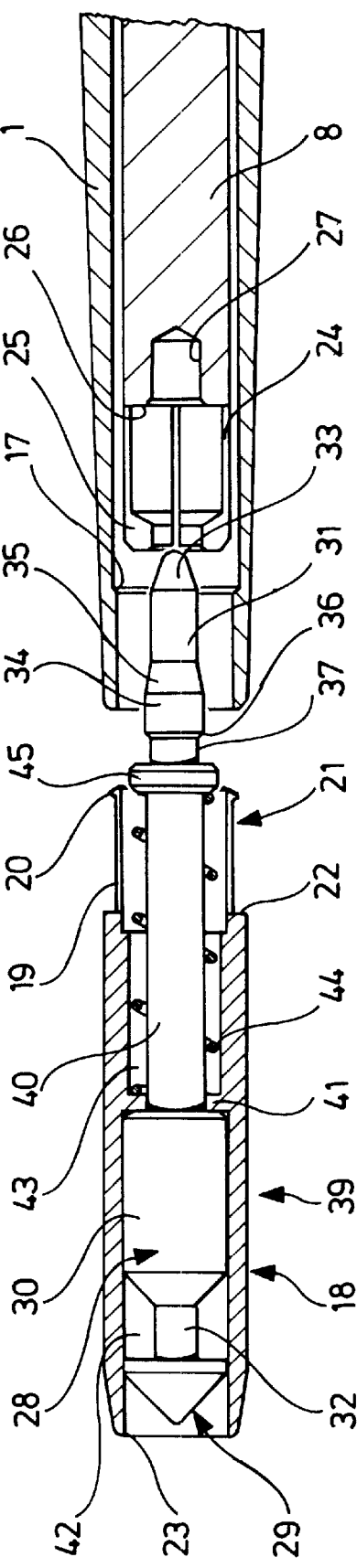
Figure 7:
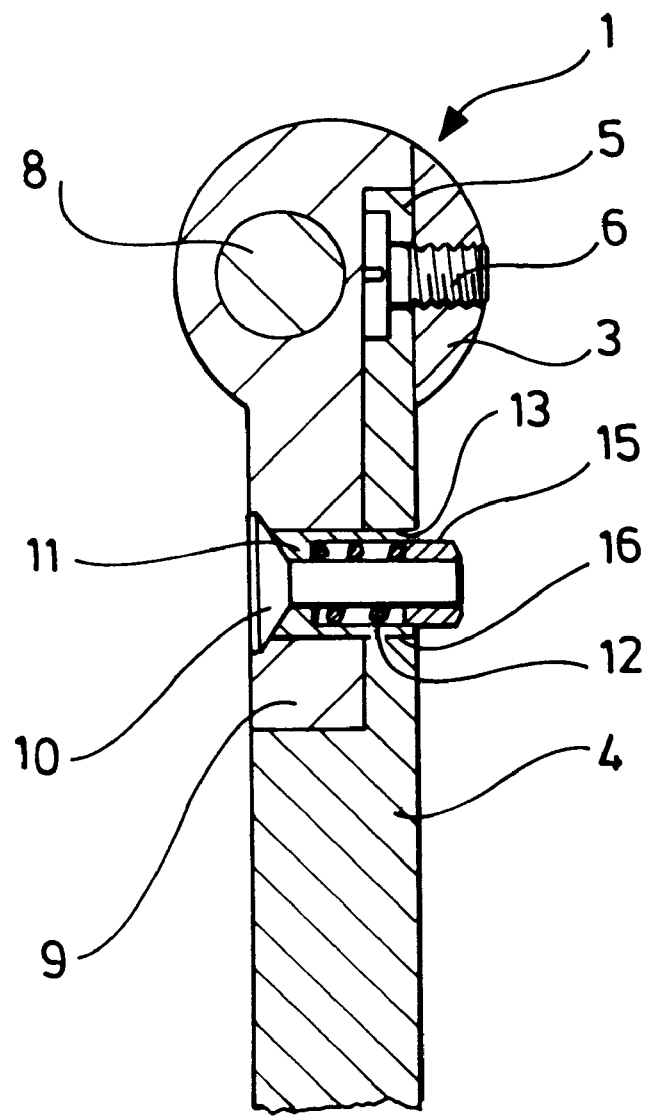

FIG. 1 a side view of a surgical punch prior to the cutting procedure, wherein an advancing element drawn back for the release of detent connections is illustrated by dash-dot lines;

FIG. 2 a view similar to FIG. 1 at the end of the cutting procedure;

FIG. 3 a longitudinal sectional view of the distal end region of the surgical punch of FIG. 1 with inserted sleeve and inserted cutting member;

FIG. 4 a view similar to FIG. 3 with sleeve removed from the shaft and cutting member removed from the advancing element;

FIG. 5 a view similar to FIG. 3 in a modified embodiment, in which sleeve and cutting member form a structural unit;

FIG. 6 a view similar to FIG. 5 with structural unit consisting of sleeve and cutting member removed and FIG. 7 a sectional view along line 7—7 in FIG. 2.

DETAILED DESCRIPTION OF THE INVENTION

The surgical punch illustrated in FIGS. 1 and 2 has a long tubular shaft 1 which is securely connected at its proximal end to a stationary branch 2. An additional branch 4 is pivotally mounted on an extension 3 of the shaft projecting laterally rearwards at the proximal end; this mounting is brought about by a hinge pin 6 penetrating a lug 5 of the branch 4 and screwed laterally into the extension 3 (FIG. 7). The two branches 2 are pressed apart from one another by a spiral spring 7 arranged between them.

An opening leads into the interior of the tubular shaft 1 next to the mounting of the pivotable branch 4. This opening is offset laterally outwards in relation to the central plane of the shaft 1 so that the mounting of the branch 4 by means of the hinge pin 6 and the opening are arranged next to one another. A rod-shaped advancing element 8 is introduced into this opening and extends essentially as far as the distal end of the shaft 1. This advancing element 8 bears at its proximal end projecting out of the opening an arm 9 which protrudes downwards and is articulatedly connected to the branch 4 at a distance from the mounting thereof effected by the hinge pin 6. This additional rotary connection is provided by a hinge pin 10 which is mounted in an opening 11 of the arm 9 for displacement in axial direction. This hinge pin 10 is displaced in the direction towards the branch 4 by a helical spring 12 surrounding it and penetrates a hinge opening 13 in it which has an insert slot 14 extending parallel to the axis of the shaft 1 in a distal direction, the width of the slot being less than the diameter of the hinge opening 13 (FIG. 1).

The hinge pin 10 has at its free end a section 15 with a smaller external diameter and following this a section 16 with a larger external diameter. The external diameter of the section 16 corresponds to the diameter of the hinge opening 13, the external diameter of the section 15 to the width of the insert slot 14.

When the hinge pin 10 is displaced under the action of the helical spring 12, the section 16 with a greater external diameter projects into the hinge opening 13 and thereby forms an articulated connection between the arm 9 and the branch 4. If the hinge pin 10 is, however, displaced contrary to the action of the helical spring 12, the section 15 with a smaller diameter moves into the plane of the hinge opening 13, and it is then possible to displace the arm 9 together with the advancing element 8 in a proximal direction, wherein the section 15 with a smaller diameter exits out of the hinge opening 13 through the insert slot 14. This displacing movement is indicated in FIG. 1 with dash-dot lines. The articulated connection between arm 9 and branch 4 can be released in this manner.

At its distal end the shaft 1 narrows in a stepped manner and forms an annular shoulder 17 in the region of transition.

A sleeve 18 bears at its end facing the shaft 1 a number of flexible tongues 19 which are aligned axis parallel and designed in one piece with the sleeve 18 and which each have at their free ends a detent projection 20 pointing outwards. The flexible tongues 19 form an insert shaft 21, the external diameter of which corresponds to the internal diameter of the shaft 1 at its distal end.

At the transition of the flexible tongues 19 into the sleeve 18 the external diameter of the sleeve 18 increases in steps; the step 22 thereby formed forms a stop. At the distal end, the sleeve 18 ends in a sharp, annular cutting edge 23.

The sleeve 18 is inserted with the flexible tongues 19 into the shaft 1 from the distal side, wherein the insert shaft 21 guides the sleeve 18 in a radial direction in the shaft 1. When the sleeve 18 is completely inserted, the flexible tongues 19 spring elastically outwards, whereby the detent projections 20 engage behind the annular shoulder 17 of the shaft 1. The sleeve 18 is thereby fixed in position in axial direction, as well, any further inserting is prevented by the step 22 coming to rest on the end face of the shaft 1, any withdrawal by the engagement of the detent projections 20 behind the annular shoulder 17. However, it is possible to remove the sleeve 18 in proximal direction when the sleeve is withdrawn forcefully since, during such a withdrawal movement, the flexible tongues 19 are moved elastically inwards so that the detent projections 20 can release the annular shoulder 17.

The sleeve 18 preferably consists of a very wear-resistant material, for example, of a hard metal so that the cutting edge 23, as a part subject to wear, is given as long an edge life as possible.

The advancing element 8 bears at its distal end axially aligned flexible tongues 24 which are likewise distributed in circumferential direction and, at their free ends, bear inwardly projecting projections 25. The flexible tongues 24 form a cage which is open at the end face and in the base 26 of which, i.e. in the end face of the advancing element 8, a central blind-end bore 27 is arranged. The flexible tongues 24 can also be formed in one piece with the advancing element 8.

These flexible tongues 24 form a holding means for a cutting member 28 which has first of all at its distal end a cone-shaped cutting section 29, following this in proximal direction a cylindrical guide section 30 and following this a holding section 31.

The cutting section 29 has the shape of a cone, the tip of which points in distal direction. The external diameter of the base surface corresponds to the diameter of the cutting edge 23 so that this cutting section 29 can be inserted into the sleeve 18 abutting on the inner wall thereof. This cone-shaped cutting section 29 forms the actual cutting tool together with the cutting edge 23.

The cutting section 29 is connected via a cylindrical, central connection piece 32 to the cylindrical guide section 30, the external diameter of which corresponds to the internal diameter of the sleeve 18.

The holding section 31 is essentially designed as a cylindrical, central extension which is beveled at the free end 33. At a distance from the end of the guide section 30, this extension bears an annular shoulder 34 which projects in a stepped manner on its side facing the guide section 30, on the side facing away therefrom, however, it merges into the extension, forming a slide-on surface 35 in the shape of a truncated cone. This annular shoulder 34 forms a circumferential groove 37 between the guide section 30 and its step-shaped end 36.

For the purpose of connecting it to the advancing element 8, the cutting member 28 is inserted with its holding section 31 into the cage of the advancing element 8 formed by the flexible tongues 24, wherein the beveled free end 33 enters the blind-end bore 27 while the projections 25 of the flexible tongues 24 pointing inwards lock into the circumferential groove 37 via the slide-on surface 35 and the annular shoulder 34 and thereby fix the cutting member 28 in position on the advancing element 8 in radial and in axial direction. As a result of a forceful withdrawal movement it is, however, possible to separate the cutting member 28 again; in this respect the flexible tongues 24 bend elastically outwards so that the projections 25 can exit from the circumferential groove 37.

When the advancing element 8 is inserted into the shaft 1 in the normal operative position, i.e. when the arm 9 is articulatedly connected to the branch 4 via the hinge pin 10, the flexible tongues 19 of the sleeve 18 and the flexible tongues 24 of the advancing element 8 abut areally on one another. As a result, the flexible tongues 19 of the sleeve 18 cannot move elastically inwards nor the flexible tongues 24 of the advancing element 8 elastically outwards, i.e. the axial fixings provided by the flexible tongues 19 and 24 are not releasable, not only the sleeve 18 but also the cutting member 28 are unreleasably fixed in position in the shaft 1 and in the advancing element 8, respectively.

As a result of pivoting the branch 4, the advancing element 8 may be displaced in relation to the shaft 1 over a certain distance; in this respect the cutting member 28 is also displaced in relation to the sleeve 18, namely from a forward initial position (FIG. 1) as far as a withdrawn cutting position (FIG. 2). In the initial position, the cutting section 29 is spaced from the cutting edge 23.

In order to provide an opening in a vascular wall, the cutting section 29 of the cutting member 28 is first of all introduced into a vessel through a cut in the wall 38 of the vessel, wherein the vascular wall 38 is drawn elastically together in the region of the connection piece 32 and is thereby arranged between the base surface of the conical cutting section 29 and the cutting edge 23.

If the branch 4 is pivoted in the direction towards the branch 2, the advancing element 8 is withdrawn in the shaft 1 in proximal direction, and as a result the cutting section 29 of the cutting member 28 is moved against the cutting edge 23. In this way an opening is punched into the wall 28, the contour of which corresponds to the contour of the cutting edge 23. The cutting section 29 can thereby be drawn slightly into the interior of the sleeve 18.

During this entire operating procedure and the relative displacement of the advancing element 8 in relation to the shaft 1 connected with it the flexible tongues 24 and the flexible tongues 19 always remain in mutual abutment so that the locking of the sleeve 18 in relation to the shaft 1 and of the cutting member 28 in relation to the advancing element 8 is maintained.

In order to release this locking, it is necessary first of all to release the articulated connection between the arm 9 and the branch 4 in the specified manner by displacing the hinge pin 10 in axial direction. Subsequently, the advancing element 8 may be moved out of the shaft 1 in proximal direction, as illustrated in FIG. 1 by dash-dot lines. As a result of this push-back movement, the flexible tongues 19 of the sleeve 18 are released so that the sleeve 18 can now be removed in distal direction in the manner described.

In order to remove the cutting member 28, the advancing element 8 is drawn completely out of the shaft 1, the flexible tongues 24 are then no longer prevented from moving elastically outwards and can release the cutting member 28.

The two detent connections are therefore locked solely as a result of insertion of the advancing element 8 into the operative position, they are released solely by the advancing element 8 being displaced in proximal direction in relation to the shaft 1.

In the embodiment of FIGS. 1 to 4, the sleeve 18 and the cutting member 28 are designed as separate parts which are also connected independently of one another to the shaft 1 and the advancing element 8, respectively.

In the embodiment of FIGS. 5 and 6, on the other hand, the sleeve 18 and the cutting member 28 form a structural unit 39. Altogether, an essentially similar construction is also chosen for this embodiment, parts corresponding to one another therefore have the same reference numerals.

In order to combine sleeve 18 and cutting member 28 to form a structural unit, i.e. to connect them undetachably to one another, a holding section 40 is inserted into the cutting member 28 between the guide section 30 and the circumferential groove 37; moreover, the sleeve 18 is of a longer design in comparison with the sleeve 18 of the embodiment of FIGS. 1 to 4. The sleeve 18 is divided by an inwardly pointing annular shoulder 41 into a distal section 42 and a proximal section 43. The distal section 42 accommodates the guide section 30 of the cutting member 28 and guides the cutting member 28 for longitudinal displacement. The proximal section 43 essentially serves to accommodate the holding section 40 of the cutting member 28. This cylindrical section is surrounded by a helical spring 44 which is supported, on the one hand, on the annular shoulder 41 and, on the other hand, on an annular shoulder 45 of the holding section 40 which is arranged to adjoin directly on the circumferential groove 37. This helical spring 44 pushes the cutting member 28 in proximal direction so that, under its action, the guide section 30 and the cutting section 29 of the cutting member 28 dip into the distal section 42 of the sleeve 18. This displacing movement is limited by the guide section 30 coming to rest on the annular shoulder 41 (FIG. 6). In the reverse direction, the displacing movement of the cutting member 28 is limited by the helical spring 44 being pressed together completely. As a result, the cutting member 28 is held undetachably in the sleeve 18.

In operative position, the connection between sleeve 18 and shaft 1, on the one hand, as well as cutting member 28 and advancing element 8, on the other hand, is brought about in exactly the same manner as in the embodiment described on the basis of FIGS. 1 to 4. In this case, as well, the flexible tongues 19 and 24 lock one another in position as a result of mutual abutment.

To release this connection it is, however, sufficient in this case to displace the advancing element 8 to such an extent in proximal direction that the flexible tongues 19 and 24 no longer overlap. In this respect, the guide section 30 dips completely into the distal section 42 of the sleeve 18. As a result of the release of the flexible tongues 19 and 24, sleeve 18 and cutting member 28 can now be removed together in such a withdrawn position of the advancing element 8; both detent connections are thereby released at the same time. The cutting member 28 is released from its connection by the annular shoulder 41 of the sleeve 18 coming to rest on the guide section 30 and taking along the cutting member 28 when the sleeve 18 is pulled out further.

Vice versa, during insertion of the structural unit 39 into the shaft 1 both detent connections are provided at the same time; the helical spring 44 thereby prevents the cutting member 28 from deviating in distal direction during insertion of the cutting member 28 between the flexible tongues 24. It is, therefore, possible to provide both detent connections during axial insertion of the sleeve 18 into the shaft 1; locking takes place as a result of the advancing element 8 being displaced in distal direction to such an extent until the flexible tongues 19 and 24 again abut on one another.

With this configuration, the sleeve 18 bearing the cutting edge 23 and the cutting member 28 can be replaced together and so two cutting tools which are adapted to one another in an optimum manner can be inserted together.

What is claimed is:

1. A surgical punch, comprising:
   a tubular shaft having a longitudinal axis, a distal end forming an annular cutting edge, and a proximal end;
   an advancing element mounted for axial displacement in said tubular shaft;
   said advancing element displaceable in said tubular shaft according to an actuating member arranged at said proximal end;
   a cutting member held on said advancing element and displaceable therewith;
   said cutting member having a cutting section adapted to move axially in an operative range to interact with said annular cutting edge when said advancing element is moved; and
   a plurality of first projections and associated first recesses arranged circumferentially to lock said cutting member in a locking position relative to said advancing element when said cutting member is in said operative range; wherein:

said plurality of first projections are elastically displaceable radially, and extend radially for engaging said first recesses when said first projections are moved axially toward said first recesses; and in said locking position of said cutting member, a distal inner circumferential wall portion of said tubular shaft prevents said plurality of first projections from moving radially away from said first recesses to a release position, wherein said first projections disengage said first recesses.

2. The surgical punch of claim 1, wherein:

said cutting member is mounted in said sleeve so as to be longitudinally displaceable therein and undetachable therefrom.

3. The surgical punch of claim 1, further comprising:

a spring for acting on said cutting member in a proximal direction of said tubular shaft; and a stop for limiting a path of displacement of said cutting member under the action of said spring.

4. The surgical punch of claim 1, wherein:

said advancing element is releasable from said actuating member; and when said advancing element is released from said actuating member, said cutting member is adapted to be moved axially by said advancing element out of said operative range toward said proximal end to a proximal inner circumferential wall portion of said tubular shaft with a diameter that is larger than a diameter of said distal inner circumferential wall portion.

5. The surgical punch of claim 1, wherein:

said cutting member comprises a cylindrical guide section; and in said operative range of said cutting member, said cylindrical guide section abuts at least one of: (a) said distal inner circumferential wall portion of said tubular shaft, and (b) an inner circumferential wall of said sleeve, while guiding said cutting member.

6. The surgical punch of claim 5, wherein said actuating member is a hand lever articulatedly connected to said tubular shaft, said punch further comprising:

a hinge connection for releasably connecting said hand lever to said advancing element.

7. The surgical punch of claim 6, wherein said hand lever comprises:

a stationary branch securely connected to said tubular shaft; and a branch pivotable against said stationary branch.

8. The surgical punch of claim 6, wherein said hinge connection comprises:

a hinge pin mounted for axial displacement in an axial direction thereof;

a part with a hinge opening receiving said hinge pin;

said hinge pin having sections with different diameters in said axial direction, including first and second sections; wherein:

said first section has a smaller diameter than said second section and passes through a radial insert slot of said hinge connection; and said second section does not pass though said radial insert slot.

9. The surgical punch of claim 1, wherein:

said actuating member is mounted at said proximal end of said tubular shaft on one side thereof;

next to a mounting of said tubular shaft on the other side thereof, an opening leads into an interior portion of said tubular shaft; and said advancing element is adapted to be inserted through said opening.

10. The surgical punch of claim 9, wherein:

said opening is offset laterally in relation to a longitudinal central plane of said tubular shaft.

11. The surgical punch of claim 10, wherein:

said annular cutting edge is arranged symmetrically to said longitudinal central plane of said tubular shaft; and said advancing element extends slightly inclined in relation to said longitudinal central plane of said tubular shaft.

12. The surgical punch of claim 1, wherein:

said plurality of first projections are carried by said advancing element; and said first recesses are provided on said cutting member.

13. The surgical punch of claim 12, wherein:

said first recesses are provided by an annular groove in said cutting member; and in said locking position of said cutting member, said first projections extend radially inward to engage in said annular groove.

14. The surgical punch of claim 12, further comprising:

a plurality of first tongues arranged circumferentially on said advancing element for holding said plurality of first projections; wherein:

said tongues are elastically displaceable radially.

15. The surgical punch of claim 14, wherein:

said first tongues are designed in one piece with said advancing element.

16. The surgical punch of claim 14, wherein:

in said locking position of said cutting member, said cutting member dips with a proximal extension into a central, end-face recess of said advancing element.

17. The surgical punch of claim 14, further comprising:

a sleeve provided at said distal end of said tubular shaft and bearing said annular cutting edge;

a plurality of second projections and associated second recesses arranged circumferentially to lock said sleeve to said tubular shaft in a locking position of said sleeve; wherein:

said second projections are elastically displaceable radially, and extend radially for engaging said second recesses when said second projections are moved axially toward said second recesses; and in said locking position of said sleeve, said actuating member prevents said second projections from moving radially away from said second recesses to a release position thereof wherein said second projections disengage said second recesses.

18. The surgical punch of claim 17, wherein:

said plurality of second projections are carried by said sleeve; and said second recesses are provided on said tubular shaft.

19. The surgical punch of claim 18, wherein:

when said sleeve and said cutting member are in said respective locking positions thereof, said distal inner circumferential wall portion of said tubular shaft abuts radially outward surfaces of said second projections, and radially inward surfaces of said second projections abut radially outward surfaces of said first projections.

20. The surgical punch of claim 17, further comprising:
a plurality of second tongues arranged circumferentially on said sleeve for holding said plurality of second projections; wherein:
said second tongues are elastically displaceable radially.

21. The surgical punch of claim 20, wherein:
when said sleeve and said cutting member are in said respective locking positions thereof, said distal inner circumferential wall portion of said tubular shaft abuts radially outward surfaces of said second tongues, and radially inward surfaces of said second tongues abut radially outward surfaces of said first projections.

22. The surgical punch of claim 1, wherein:
said plurality of first projections are carried by said cutting member; and
said first recesses are provided on said advancing element.

23. The surgical punch of claim 22, further comprising:
a plurality of first tongues arranged circumferentially on said cutting member for holding said plurality of first projections; wherein:
said first tongues are elastically displaceable radially.

24. The surgical punch of claim 1, further comprising:
a sleeve provided at said distal end of said tubular shaft and bearing said annular cutting edge;
a plurality of second projections and associated second recesses arranged circumferentially to lock said sleeve to said tubular shaft in a locking position of said sleeve; wherein:
said second projections are elastically displaceable radially, and extend radially for engaging said second recesses when said second projections are moved axially toward said second recesses; and
in said locking position of said sleeve, said actuating member prevents said second projections from moving radially away from said second recesses to a release position thereof wherein said second projections disengage said second recesses.

25. The surgical punch of claim 24, wherein:
said plurality of second-projections are carried by said sleeve; and
said second recesses are provided on said tubular shaft.

26. The surgical punch of claim 25, wherein:
said first and second projections abut on one another when said cutting member is in at least a portion of said operative range and thereby prevent one another from moving into the release positions thereof.

27. The surgical punch of claim 25, further comprising:
a plurality of second tongues arranged circumferentially on said sleeve for holding said plurality of second projections; wherein:
said second tongues are elastically displaceable radially.

28. The surgical punch of claim 27, wherein:
said second tongues form an insert shaft that is insertable into said tubular shaft.

29. The surgical punch of claim 28, wherein:
said second tongues are designed in one piece with said sleeve.

30. The surgical punch of claim 25, wherein:
said second recesses are formed by an annular shoulder on said distal inner circumferential wall portion of said tubular shaft.

31. The surgical punch of claim 30, wherein:
said advancing element is releasable from said actuating member;
when said advancing element is released from said actuating member, said cutting member is adapted to be moved axially by said advancing element out of said operative range toward said proximal end to a proximal inner circumferential wall portion of said tubular shaft with a diameter that is larger than a diameter of said distal inner circumferential wall portion; and
said annular shoulder is adjoined in a proximal direction of said tubular shaft by said proximal inner circumferential wall portion.

32. A surgical punch, comprising:
a tubular shaft having a longitudinal axis, a distal end forming an annular cutting edge, and a proximal end;
a sleeve provided at said distal end of said tubular shaft and bearing said annular cutting edge;
a plurality of projections arranged circumferentially on said sleeve for locking said sleeve to said tubular shaft in a locking position of said sleeve; wherein:
said plurality of projections are elastically displaceable radially, and extend radially for engaging recesses in said tubular shaft when said projections are moved axially toward said recesses.

33. The surgical punch of claim 32, further comprising:
a plurality of tongues arranged circumferentially on said sleeve for holding said plurality of projections; wherein:
said tongues are elastically displaceable radially.

* * * * *